(12) United States Patent
Yamaguchi et al.

(10) Patent No.: US 6,313,357 B1
(45) Date of Patent: Nov. 6, 2001

(54) METHOD FOR RECOVERING FLUOROALCOHOL

(75) Inventors: Fumihiko Yamaguchi; Toshiyuki Katsube, both of Settsu (JP)

(73) Assignee: Daikin Industries, Ltd., Osaka-fu (JP)

(*) Notice: Subject to any disclaimer, the term of this patent is extended or adjusted under 35 U.S.C. 154(b) by 0 days.

(21) Appl. No.: 09/444,401

(22) Filed: Nov. 22, 1999

(30) Foreign Application Priority Data

Apr. 7, 1999 (JP) .................................................. 11-099867

(51) Int. Cl.⁷ .................................................... C07C 31/34
(52) U.S. Cl. ............................................................... 568/842
(58) Field of Search ............................................... 568/842

(56) References Cited

U.S. PATENT DOCUMENTS 2,559,628   7/1951   Joyce, Jr. .
4,224,112   9/1980   Childs .
4,405,409   9/1983   Tusel et al. .
4,910,344   3/1990   Pasternak et al. .

OTHER PUBLICATIONS

Bonera et al. Chem. Abst. 118:72835, 1992.*

* cited by examiner

*Primary Examiner*—Peter O'Sullivan
(74) *Attorney, Agent, or Firm*—Larson & Taylor PLC

(57) ABSTRACT

In a method for recovering a fluoroalcohol from a mixture comprising a fluoroalcohol and water, (i) a method for recovering a fluoroalcohol by distilling the mixture comprising the fluoroalcohol and water to separate water as an azeotropic or azeotrope-like composition; and (ii) a method for recovering a fluoroalcohol, wherein water is separated by pervaporation.

3 Claims, No Drawings

METHOD FOR RECOVERING FLUOROALCOHOL

TECHNICAL FIELD

The present invention relates to a method for recovering a fluoroalcohol.

BACKGROUND ART

Fluoroalcohols have high solubility in water. When water is accidentally introduced into the fluoroalcohol or water is formed during the production process of the fluoroalcohols, water and fluoroalcohols are mixed together and thus difficult to separate water from the fluoroalcohols. In addition, since the fluoroalcohols have higher coefficient of global warming than carbon dioxide, it is desirable that the alcohols are recovered after use and recycled. The fluoroalcohols, however, are highly hygroscopic and absorb moisture in the air when handled or left in the open system. Therefore, water is likely to enter into fluoroalcohols by the time it is recycled. When the fluoroalcohols are used as solvents to dissolve dyes for producing information recording media such as CD-R and DVD-R, wherein recording layers capable of writing and/or reading are provided on their substrate by means of a laser, the water contained therein may cause deterioration and impaired solubility of the dyes, leading to degraded quality of the information recording media. Consequently, when the fluoroalcohols contain water, particularly when the fluoroalcohols are recycled, the alcohols have to be purified to a level substantially free of water.

An object of the present invention is to provide a method for recovering a fluoroalcohol which is substantially free of water by separating water from a mixture comprising a fluoroalcohol and water.

DISCLOSURE OF THE INVENTION

The inventors found the followings: By the distillation of water-containing fluoroalcohol, water is distilled off as an azeotropic or azeotrope-like composition; the remaining fluoroalcohol has a very low water content; and thus a fluoroalcohol which is substantially free of water can be easily recovered.

In addition, the inventors found that a fluoroalcohol substantially free of water can also be obtained by pervaporation to separate a fluoroalcohol and water. The present invention has been accomplished based on the findings.

The present invention provides the processes and a fluoroalcohol listed below:

1. A method for recovering a fluoroalcohol from a mixture comprising a fluoroalcohol and water, wherein the fluoroalcohol is recovered by distilling the mixture of a fluoroalcohol and water to separate water as an azeotropic or azeotrope-like composition.
2. The method according to item 1, wherein the distillation is carried out under reduced pressure.
3. The method according to item 1, wherein the fluoroalcohol is represented by the formula (1)

wherein n=1 or 2; when n=1, $R^1$ represents F or $CF_3$; when n=2, $R^1$ represents F.

4. A fluoroalcohol obtained by the method of item 1, the fluoroalcohol containing not more than 2,000 mass ppm of water.
5. A method for recovering a fluoroalcohol from a mixture comprising a fluoroalcohol and water, wherein water is separated by pervaporation to recover the fluoroalcohol.
6. The method according to item 5, wherein the mixture comprising the fluoroalcohol and water is an azeotropic or azeotrope-like composition of a fluoroalcohol and water.
7. The method according to item 5, wherein the pervaporation is carried out by using a membrane made of a polyamide, polyvinyl alcohol, polyacrylic ester, cellulose, perfluorosulfonic acid ionomer, chitosan, polyimide, PDMS, PBAA, PTFE, PEBA, silica or zeolite.
8. The method according to item 5, wherein the fluoroalcohol is represented by the formula (1)

wherein n=1 or 2; when n=1, $R^1$ represents F or $CF_3$; when n=2, $R^1$ represents F.

9. A fluoroalcohol obtained by the method of item 5, the fluoroalcohol containing not more than 2,000 mass ppm of water.
10. A process for recovering a fluoroalcohol comprising the steps of recovering the fluoroalcohol by distilling the mixture comprising the fluoroalcohol and water to separate water as an azeotropic or azeotrope-like composition; and separating the water contained in the separated azeotropic or azeotrope-like composition by pervaporation to recover the fluoroalcohol contained in the composition.

The fluoroalcohol is not specifically limited insofar as the alcohol has at least one fluorine atom. Examples of the preferably fluoroalcohols are those represented by the formula (1) $H(CFR^1CF_2)_nCH_2OH$ (wherein n =1 or 2; when n=1, $R^1$ represents F or $CF_3$; when n=2, $R^1$ represents F).

The amount of the fluoroalcohol contained in the mixture subjected to distillation is more than the amount of the fluoroalcohol in the azeotropic or azeotrope-like composition of the fluoroalcohol and water. The content of fluoroalcohol is typically 80 mass % or more, preferably 90 mass % or more, based on the total weight of the mixture. When the mixture is separated into two phases (i.e., aqueous phase and organic phase), the organic phase may be subjected to distillation.

For example, when the fluoroalcohol is $HCF_2CF_2CH_2OH$ (in the formula (1), n=1 and $R^1$=F), $HCF_2CF_2CH_2OH$ and water form a homogeneous solution. The azeotropic composition of $HCF_2CF_2CH_2OH$ : water has a ratio of 72.5:27.5 (by weight) (azeotropic point: 92.5° C., at atmospheric pressure). Therefore, by the distillation of the mixture containing more than 72.5 mass %, preferably more than 90 mass % of $HCF_2CF_2CH_2OH$, water is distilled off with the fluoroalcohol as an azeotropic or azeotrope-like composition. Thus, $HCF_2CF_2CH_2OH$ free of water is recovered from the mixture.

As to $HCF_2CF_2CF_2CF_2CH_2OH$ (in the formula (1), n=2 and $R^1$=F), $HCF_2CF_2CF_2CF_2CH_2OH$ and water is separated into two phases when the content of $HCF_2CF_2CF_2CF_2CH_2OH$ in the mixture is at least 2.9 mass % and not more than 94.2 mass %. $HCF_2CF_2CF_2CF_2CH_2OH$ and water are uniformly mixed when the content of $HCF_2CF_2CF_2CF_2CH_2OH$ is outside the above range (at 25° C.). The azeotropic composition of $HCF_2CF_2CF_2CF_2CH_2OH$ : water has a ratio of 62.0:38.0 (by weight) (azeotropic point: 97.8° C., at an atmospheric pressure). Therefore, by the distillation of the mixture (including the separated organic phase) wherein $HCF_2CF_2CF_2CF_2CH_2OH$ and water are uniformly mixed, water is distilled off with the fluoroalcohol as an azeotropic or azeotrope-like composition. Thus, $HCF_2CF_2CF_2CH_2OH$ free of water is recovered from the mixture.

As to $CF_3CHFCF_2CH_2OH$ (in the formula (1), n=1 and $R^1=CF_3$), $CF_3CHFCF_2CH_2OH$ and water is separated into two phases when content of $CF_3CHFCF_2CH_2OH$ in the mixture is at least 7.5 mass % and not more than 90.4 mass %. $CF_3CHFCF_2CH_2OH$ and water are uniformly mixed when the content of $CF_3CHFCF_2CH_2OH$ is outside the above range (at 25° C.). The azeotropic composition of $CF_3CHFCF_2CH_2OH$: water has a ratio of 75.0:25.0 (by weight) (azeotropic point: 94.2° C., at an atmospheric pressure). Therefore, by the distillation of the mixture (including the separated organic phase) wherein $CF_3CHFCF_2CH_2OH$ and water are uniformly mixed, water is distilled off with the fluoroalcohol as an azeotropic or azeotrope-like composition. Thus, $CF_3CHFCF_2CH_2OH$ free of water is recovered from the mixture.

An azeotropic composition herein means a composition whose vapor, being in equilibrium with a liquid mixture, has the same ratio as the liquid mixture. An azeotrope-like composition means a composition whose vapor, being in equilibrium with a liquid mixture, has a similar ratio as the liquid mixture.

Distillation is carried out at ambient pressure or under reduced pressure, for example, about 0.001–0.1 MPa. Furthermore, the distillation under determined pressure is carried out at an azeotropic temperature, typically at about 30–98° C.

After being separated by distillation, a fluoroalcohol substantially free of water can be obtained by collecting the fluoroalcohol remaining in the distillation still.

The membrane for use in pervaporation may be suitably selected from the conventional membranes used in pervaporation depending on the types of the fluoroalcohol etc. The materials of the membrane may be, for example, polyamides, polyvinyl alcohols, polyacrylic esters, cellulose, perfluorosulfonic acid ionomer, chitosan, polyimides, PDMS (polydimethylsiloxane), PBAA (polyvinylbutylate-acrylic acid copolymer), PTFE (polytetrafluoroethylene), PEBA (polyethylene-butyl acrylate copolymer) and like organic polymers; and silica, zeolite and like ceramics. A preferable perfluorosulfonic acid ionomer membrane is "Nafion" (trademark, E. I. du Pont de Nemours and Company, U.S.A.)

The shape of the membrane is not specifically limited and generally in the form of a sheet, a film or a tube. The thickness of the membrane is suitably determined depending on the material and form of the membrane, etc. The thickness is typically about 10–200 μm, preferably about 20–150 μm.

Separation by pervaporation is carried out using a conventional membrane separation apparatus equipped with the above-described membrane by placing the mixture comprising the fluoroalcohol and water on the primary side (high-pressure side). The mixture which is subjected to pervaporation may be the azeotropic or azeotrope-like composition of the fluoroalcohol and water obtained by the distillation of the mixture comprising the fluoroalcohol and water. For example, the mixture comprising the fluoroalcohol and water is distilled to remove water as an azeotropic or azeotrope-like composition, and then the removed azeotropic or azeotrope-like composition containing water and the fluoroalcohol may be subjected to pervaporation. When the mixture is separated into two phases (i.e., organic phase and aqueous phase), each phase may be subjected to distillation, and the azeotropic or azeotrope-like composition obtained by the distillation of the organic phase or aqueous phase may also be subjected to the pervaporation.

The conditions for the separation by pervaporation are suitably selected depending on the types of the fluoroalcohol. Typically, the primary side is pressurized to atmospheric pressure to about 10 MPa, while the secondary side (low-pressure side) is depressurized to reduced pressure of about 0.00001–0.1 MPa or maintained at atmospheric pressure, and the separation is carried out at about 10–80° C. for about 0.1–10 hours, preferably about 0.5–5 hours. The liquid remaining on the primary side is collected to obtain a fluoroalcohol which is substantially free of water.

The recovery method by pervaporation is especially useful when a large amount of water is contained in the mixture, e.g., more than 5 mass % of water is contained, compared with the recovery by distillation. When a large amount of water is contained in the mixture, recovery by distillation increases the proportion of the fluoroalcohol which is separated out along with water as an azeotropic or azeotrope-like composition, and thus decreases the proportion of the remaining fluoroalcohol to be collected. In contrast, even when a large amount of water is contained in the mixture, the recovery by pervaporation is useful because such decrease in the yield of the fluoroalcohol does not occur. The upper value of the water content is not specifically limited and is preferably not higher than 30 mass %, more preferably not higher than 10 mass %. When the mixture is separated into two phases, each phase may be subjected to the pervaporation to recover the fluoroalcohol.

In the present invention, by the expression that the fluoroalcohol is "substantially free of water" is meant that the fluoroalcohol contains not more than 2,000 mass ppm, preferably not more than 1,000 mass ppm of water.

According to the present invention, water is easily separated from a fluoroalcohol and a fluoroalcohol substantially free of water can be recovered. Therefore, when recycled as a solvent for producing information recording media such as CD-R and DVD-R, the highly purified fluoroalcohol does not degrade the quality of the information recording media produced.

BEST MODE FOR CARRYING OUT THE INVENTION

The present invention is explained in more detail with the examples given below. It is to be understood that the present invention is not limited to the examples shown herein.

EXAMPLE 1

$HCF_2CF_2CH_2OH$ (500 g) containing 3 mass % of water was placed in a glass flask (1 L) equipped with a thermometer, a stirrer and a fractionation apparatus, and was fractionated at ambient pressure, and a distillate (b.p.;80–105° C., 76 g) was separated. The liquid remaining in the flask was analyzed by Karl Fischer method and gas chromatography and found to be $HCF_2CF_2CH_2OH$ having a purity of 99.9 mass % and containing 1,200 mass ppm of water.

EXAMPLE 2

$HCF_2CF_2CH_2OH$ (500 g) containing 3 mass % of water was placed in a membrane separation apparatus equipped with a pervaporation membrane made of a polyamide resin (about 100 μm in thickness) and a stirrer. The apparatus was heated to 70° C. and the secondary side of the pervaporation membrane was depressurized to 1.33 hPa (1 mmHg) using a vacuum pump via a liquid nitrogen trap. Five hours later, the secondary side was returned to ambient pressure, and then a liquid (22 g) containing water in the concentration of 70 mass % or higher was collected from the liquid nitrogen trap. The liquid remaining at the primary side of the membrane separation apparatus was analyzed by Karl Fischer method and gas chromatography and found to be $HCF_2CF_2CH_2OH$ having a purity of 99.9 mass % and containing 1,850 mass ppm of water.

EXAMPLE 3

The procedure of Example 1 was repeated with the exception of using $HCF_2CF_2CF_2CF_2CH_2OH$ in place of $HCF_2CF_2CH_2OH$ to distill out 84 g of a distillate (b.p.; 90–135° C.). The liquid remaining in the flask was analyzed in the same manner as in Example 1 and found to be $HCF_2CF_2CF_2CF_2CH_2OH$ having a purity of 99.9 mass % and containing 950 mass ppm of water.

EXAMPLE 4

Pervaporation was carried out following the procedure of Example 2 with the exception of using $HCF_2CF_2CF_2CF_2CH_2OH$ in place of $HCF_2CF_2CH_2OH$ and a pervaporation membrane made of zeolite which was about 30 μm in thickness in place of the membrane made of polyamide resin. A liquid containing water in the concentration of 70 mass % or higher was collected from the liquid nitrogen trap. The liquid remaining at the primary side of the membrane separation apparatus was analyzed in the same manner as in Example 2 and found to be $HCF_2CF_2CF_2CF_2CH_2OH$ having a purity of 99.9 mass % and containing 850 mass ppm of water.

EXAMPLE 5

Pervaporation was carried out following the procedure of Example 2 with the exception of using a pervaporation membrane made of a polyvinyl alcohol which was about 150 μm in thickness in place of the membrane made of polyamide resin. A liquid containing water in the concentration of 80 mass % or higher was collected from the liquid nitrogen trap. The liquid remaining at the primary side of the membrane separation apparatus was analyzed in the same manner as in Example 2 and found to be $HCF_2CF_2CH_2OH$ having a purity of 99.9 mass % and containing 1,900 mass ppm of water.

EXAMPLE 6

Pervaporation was carried out following the procedure of Example 2 with the exception of using $CF_3CHFCF_2CH_2OH$ in place of $HCF_2CF_2CH_2OH$ and a pervaporation membrane made of cellulose which was about 50 μm in thickness in place of the membrane made of polyamide resin. A liquid containing water in the concentration of 90 mass % or higher was collected from the liquid nitrogen trap. The liquid remaining at the primary side of the membrane separation apparatus was analyzed in the same manner as in Example 2 and found to be $CF_3CHFCF_2CH_2OH$ having a purity of 99.9 mass % and containing 1,000 mass ppm of water.

EXAMPLE 7

Water (500g) was added to 500 g of $HCF_2CF_2CF_2CF_2CH_2OH$. As a result, the mixture was separated into two phases. The organic phase (lower phase) was recovered and 512.67 g of organic liquid was obtained. The procedure of Example 1 was repeated with the exception of using the organic liquid in place of $HCF_2CF_2CH_2OH$ containing 3 mass % of water to distill out 130 g of a distillate $HCF_2CF_2CF_2CF_2CH_2OH$ (b.p.; 90–135° C.). The liquid remaining in the flask was analyzed in the same manner as in Example 1 and found to be $HCF_2CF_2CF_2CF_2CH_2OH$ having a purity of 99.9 mass % and containing 1,000 mass ppm of water.

EXAMPLE 8

Water (500g) was added to 500 g of $CF_3CHFCF_2CH_2OH$. As a result, the mixture was separated into two phases. The organic phase was recovered and 515.88 g of organic liquid was obtained. The procedure of Example 1 was repeated with the exception of using the organic liquid in place of $HCF_2CF_2CH_2OH$ containing 3 mass % of water to distill out 120 g of a distillate $CF_3CHFCF_2CH_2OH$ (b.p.; 80–110° C.). The liquid remaining in the flask was analyzed in the same manner as in Example 1 and found to be $CF_3CHFCF_2CH_2OH$ having a purity of 99.9 mass % and containing 1,000 mass ppm of water.

What is claimed is:

1. A method for recovering a fluoroalcohol from a mixture comprising a fluoroalcohol and water, wherein the fluoroalcohol is recovered by distilling the mixture of a fluoroalcohol and water to separate water as an azeotropic or azeotrope-like composition, the fluoroalcohol being represented by the formula (1)

$$H(CF_2CF_2)_nCH_2OH \tag{1}$$

wherein n=1 or 2.

2. The method according to claim 1, wherein the distillation is carried out under reduced pressure.

3. A process for recovering a fluoroalcohol comprising the steps of recovering the fluoroalcohol by distilling the mixture comprising the fluoroalcohol and water to separate water as an azeotropic or azeotrope-like composition; and separating the water contained in the separated azeotropic or azeotrope-like composition by pervaporation to recover the fluoroalcohol contained in the composition, the fluoroalcohol being represented by the formula (1)

$$H(CF_2CF_2)_nCH_2OH \tag{1}$$

wherein n=1 or 2.

* * * * *